(12) United States Patent
Naluai et al.

(10) Patent No.: US 7,536,913 B2
(45) Date of Patent: May 26, 2009

(54) RIGIDLY MOUNTED UNDERWATER ACOUSTIC INERTIAL VECTOR SENSOR

(75) Inventors: Nathan K. Naluai, State College, PA (US); Gerald C. Lauchle, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 265 days.

(21) Appl. No.: 11/264,421

(22) Filed: Nov. 1, 2005

(65) Prior Publication Data

US 2006/0236772 A1  Oct. 26, 2006

Related U.S. Application Data

(60) Provisional application No. 60/630,676, filed on Nov. 23, 2004.

(51) Int. Cl.
*G01N 29/036* (2006.01)
*G01P 15/09* (2006.01)
*G01V 1/145* (2006.01)
*G10K 11/00* (2006.01)

(52) U.S. Cl. .............. 73/633; 73/514.34; 367/141; 367/153

(58) Field of Classification Search ........... 73/633, 73/514.34; 367/141, 153, 154, 155
See application file for complete search history.

(56) References Cited

U.S. PATENT DOCUMENTS

| | | | |
|---|---|---|---|
| 2,582,994 A | 1/1952 | Kendall | 177/352 |
| 3,311,873 A | 3/1967 | Schloss | 340/10 |
| 4,982,375 A | 1/1991 | Ng | 367/135 |
| 5,322,390 A * | 6/1994 | Niimura | 405/136 |
| 5,392,258 A | 2/1995 | Gabrielson et al. | 367/149 |
| 6,172,940 B1 | 1/2001 | McConnell et al. | 367/178 |
| 6,275,448 B1 | 8/2001 | Kittower et al. | |
| 6,370,084 B1 | 4/2002 | Cray | 367/141 |
| 6,545,948 B1 | 4/2003 | Jiang | |
| 6,697,302 B1 * | 2/2004 | Cray et al. | 367/141 |
| 7,054,228 B1 | 5/2006 | Hickling | |
| 7,066,026 B2 | 6/2006 | Deng | |
| 7,206,258 B1 * | 4/2007 | Fisher et al. | 367/141 |
| 7,292,501 B2 * | 11/2007 | Barger | 367/118 |

\* cited by examiner

*Primary Examiner*—Hezron Williams
*Assistant Examiner*—J M Saint Surin
(74) *Attorney, Agent, or Firm*—Gifford, Krass, Sprinkle, Anderson & Citkowski, P.C.

(57) ABSTRACT

An underwater acoustic sensor is designed for attachment to a rigid or semi-rigid mounting structure. The sensor includes an outer casing and a secondary casing spaced therefrom. A compliance layer is disposed between the inner surface of the outer casing and the outer surface of the secondary casing. An inner sensor support is designed to attach to the mounting structure and is spaced from the inner surface of the secondary casing. A plurality of sensor elements are disposed between and interconnect the inner surface of the secondary casing and the sensor support.

21 Claims, 4 Drawing Sheets

RIGIDLY MOUNTED UNDERWATER ACOUSTIC INERTIAL VECTOR SENSOR

REFERENCE TO RELATED APPLICATION

This application claims priority from U.S. Provisional Patent Application Ser. No. 60/630,676, filed Nov. 23, 2004, the entire content of which is incorporated herein by reference.

STATEMENT OF GOVERNMENT INTEREST

The invention described herein was made with Government support under Contract No. N00014-03-1-0863 awarded by the Office of Naval Research. The United States Governmental has certain rights in this invention.

FIELD OF THE INVENTION

The present invention relates generally to underwater acoustic sensors.

BACKGROUND OF THE INVENTION

Conventional underwater probes are suspended in a body of water, carried onboard a vessel, or are allowed to rest upon the floor of a body of water. The measurements that these probes provide can be used to determine the nature of noise emission from underwater sources such as those generated from natural (weather, geological, or biologically-related) or man-made processes. For instance, the probes can be used to detect distant vessels, perform seismic surveys, monitor ambient noise in the sea, aid in fish localization, or aid in fossil fuel exploration. Such probes can also be used to assess the effectiveness and directionality of radiation from underwater sources.

An acoustic intensity measurement provides an indication of the vector energy flux density of an acoustic field. Acoustic intensity is the product of acoustic particle velocity, $\vec{u}$, and acoustic pressure, p. There are two primary probe design types known in the art for measuring underwater acoustic intensity: pressure-gradient probes and inertial probes.

The most commonly used design is the pressure-gradient probe. Such a probe is described in U.S. Pat. No. 4,982,375. This probe consists of two hydrophones fixed a distance $\Delta r$ apart. One key advantage of this design type is that the hydrophones can be rigidly fixed in space (motion is not central to sensing). The sum of the outputs provides a direct measurement of the acoustic pressure at the midpoint of the hydrophones. Although the acoustic velocity is not directly measured using this technique, it can be determined using a finite-difference approximation to the velocity, given as:

$$u_r \approx j \frac{\Delta p}{\omega \rho \Delta r}$$

where $u_r$ is the acoustic velocity; $\Delta p$ is the difference between the hydrophone outputs; $\rho$ is the density of water; and $\omega$ is the radian frequency. The acoustic intensity is then determined as the time-averaged product of the acoustic pressure and velocity.

The pressure-gradient probe has several inherent disadvantages. The derived velocity is a function of frequency, and therefore, each spectral component to be studied must be weighted differently to compensate for the frequency dependence. The distance the hydrophones are set apart can cause inaccurate measurements. Setting the hydrophones too closely together greatly decreases the dynamic range of the probe. Setting the hydrophones too far apart can result in the inaccurate measurement of acoustic fields which depart from perfect plane wave behavior.

A second design type which is rapidly gaining popularity in the art is the inertial probe design. The output of an inertial probe is directly related to the motion of the probe body. Two such probes are described in U.S. Pat. Nos. 5,392,258 and 6,172,940. The probe of U.S. Pat. No. 5,392,258 measures the acoustic particle velocity directly from the output of a geophone encased in a neutrally buoyant syntactic foam cylindrical body. The probe is suspended such that motion in directions other than the primary sensing direction of the geophone is suppressed. Pressure hydrophones, attached to the end caps of the cylinder, are spatially averaged to yield acoustic pressure. The product of the averaged hydrophone output and the velocity sensor output is directly proportional to the acoustic intensity. U.S. Pat. No. 6,172,940 combines the inertial probe design above with the gradient technique. Two geophones are encased in independent, neutrally buoyant bodies and set a fixed distance, $\Delta r$, apart. The average of the two geophone signals gives a signal proportional to the particle velocity at the midpoint of the line separating the two geophones. In this case, the acoustic pressure is not directly measured, but again it can then be determined using the measured geophone output signals.

Other inertial-type probes which claim to directly measure underwater acoustic intensity are disclosed in U.S. Pat. Nos. 3,311,873 and 2,582,994. The probe of U.S. Pat. No. 3,311,873 directly measures both acoustic pressure and acoustic acceleration electrically integrated to determine velocity. The probe of U.S. Pat. No. 2,582,994 is an air-tight, rigid, metal sphere encapsulating an acoustic velocity sensor. While both of these probes may potentially measure acoustic intensity, the probe of U.S. Pat. No. 3,311,873 disregards the inertial effects of water which seriously impedes the motion of the sensor to an acoustic force and the probe of U.S. Pat. No. 2,582,994 is extremely large and perturbs the acoustic field to a significant degree, causing scattering of wave motion.

In any embodiment of an inertial probe design, suspension design is critical, since the signal output is proportional to the motion of the probe body. Fundamentally, the suspension must fix the time-averaged position of the probe while permitting movement of the sensor body with the acoustic force. It should have a natural frequency well below the intended range of operation. Finally, it must not distort the probe response in magnitude or phase. For single-dimension probes, as in U.S. Pat. Nos. 5,392,258 and 6,172,940, suspension designs are straightforward. Two-dimensional probes are much more common in underwater acoustics. In this case, probe motion can be restricted to be planar with the third axis used as a support axis. The navy class Directional Frequency Analysis and Recording (DIFAR) sonobouy does this by supporting the probe vertically in the water column from a taut cable connected to a surface float package, allowing unconstrained motion in the sensing plane (a plane normal to the suspension cable and parallel to the water surface).

Designs sensitive in three-dimensions are difficult to build without significantly affecting the probe's response. U.S. Pat. No. 6,370,084 describes a three-axis inertial type probe encased in a viscoelastic rubber which serves as the suspension. However, special care must be exercised in the design of the shear stiffness of such a suspension. If the design relies on shear stiffness to control the suspension resonance, the mount must be designed to avoid any axis being constrained by compression of the material since the compressional modulus is normally much higher. With such a system, it is extremely difficult to avoid considerable anisotropy in the suspension.

SUMMARY OF THE INVENTION

Preferred embodiments of the present invention provide a probe for measuring underwater sounds with a suspension method for a neutrally buoyant inertial probe used to directly measure true underwater acoustic intensity which is a vector quantity. These embodiments allow for the measurement of the vector components of the underwater intensity generated by some source of interest with a single, self-contained probe that is rigidly mounted to an external support structure.

In contrast with the probes of the prior art, a neutrally buoyant probe according to preferred embodiments of the present invention directly measure both acoustic velocity and pressure. More importantly, the some embodiments of the invention provide a probe whose dynamics are such that motion of a central support rod is essentially zero in the frequency band of interest. Consequently, the rod can be rigidly mounted to an existing support structure with no effect on the probe's response to acoustic excitation. The probe provides for a true acoustic intensity measurement of greater accuracy, in all types of acoustic fields, at higher frequencies than allowed by prior probe designs. The probe body also can be made more compact than that of the prior art, thereby reducing the scattering effect of the body of the probe at those frequencies. Further, the invention design preferably provides an underwater probe which accurately measures acoustic intensity at frequencies above 20 kHz with a sensitivity to acoustic pressure fluctuations as small as 25 dB re 1 µPa (approx. Sea-state Zero).

According to one embodiment of the present invention, an underwater acoustic sensor is provided for attachment to a rigid or semi-rigid mounting structure. The sensor includes a generally rigid outer casing having an inner surface and an outer surface. A generally rigid secondary casing is spaced from the outer casing and has an inner surface and an outer surface. A compliance layer is disposed between the inner surface of the outer casing and the outer surface of the secondary casing. An inner sensor support is configured for attachment to the mounting structure. The sensor support is spaced from the inner surface of the secondary casing. A plurality of sensor elements are disposed between and interconnect the inner surface of the secondary casing and the sensor support. In some versions, the sensor elements are piezoelectric elements and some may be poled to sense shear and some may be poled to sense compression or tension. In some versions, the sensor elements comprise a system of independent pairs or groups of piezoelectric elements operable to provide a signal proportional to the three independent orthogonal components of acoustic particle velocity due to the motion of the outer casing.

The sensor element has a useful frequency range and the resonance frequency of the outer casing, compliant layer and secondary casing is preferably lower than the useful frequency range. In further versions, the outer casing and the secondary casing are cylindrical, rectangular or spherical, and the sensor support may have a generally rectangular outer surface. The compliance layer may be a layer of compliant material, such as silicon rubber.

In yet further versions, the outer casing is neutrally buoyant. The outer casing may include a generally rigid inner portion and a generally rigid foam covering at least a part of the inner portion. The sensor may also include a pressure sensor disposed on the outer surface of the outer casing. The outer casing may be generally cylindrical with a pair of opposed end faces with a pressure sensor disposed on each of the opposed end faces. As yet a further alternative, the outer casing may be at least partially formed of a piezoelectric material such that it is operable as a pressure sensor. The sensor may also include circuitry for processing signals from the sensor elements. The sensor support may be the outer surface of the rigid or semi-rigid mounting structure.

According to another embodiment of the present invention, an underwater acoustic sensor designed for attachment to a rigid or semi-rigid mounting structure includes a generally rigid outer casing having an inner surface and an outer surface. A generally rigid secondary casing is spaced from the outer casing and has an inner surface and an outer surface. A plurality of sensor elements are disposed between and interconnect the inner surface of the outer casing and the outer surface of the secondary casing. An inner sensor support is configured for attachment to the mounting structure and is spaced from the inner surface of the secondary casing. A compliance layer is disposed between the inner surface of the secondary casing and the sensor support. In some versions, the combination of the outer casing, the inner casing and the sensor elements is neutrally buoyant. A pressure sensor may be disposed on the outer surface of the outer casing. Alternatively, the outer casing may be at least partially formed of a piezoelectric material such that it is operable as a pressure sensor.

According to yet another embodiment of the present invention, an underwater sensor array includes a mounting structure having an outer surface and a plurality of underwater sensors disposed on the mounting structure. Each sensor includes a generally rigid outer casing having an inner surface and an outer surface. A generally rigid secondary casing is spaced from the outer surface and has an inner surface and an outer surface. A compliance layer is disposed between the inner surface of the outer casing and the outer surface of the secondary casing. A plurality of sensor elements are disposed between and interconnect the inner surface of the secondary casing and the outer surface of the mounting structure.

Other objects, advantages and novel features of the invention will become apparent from the following detailed description of the invention when considered in conjunction with the accompanying drawings.

DESCRIPTION OF THE PREFERRED EMBODIMENTS

Figure 1:
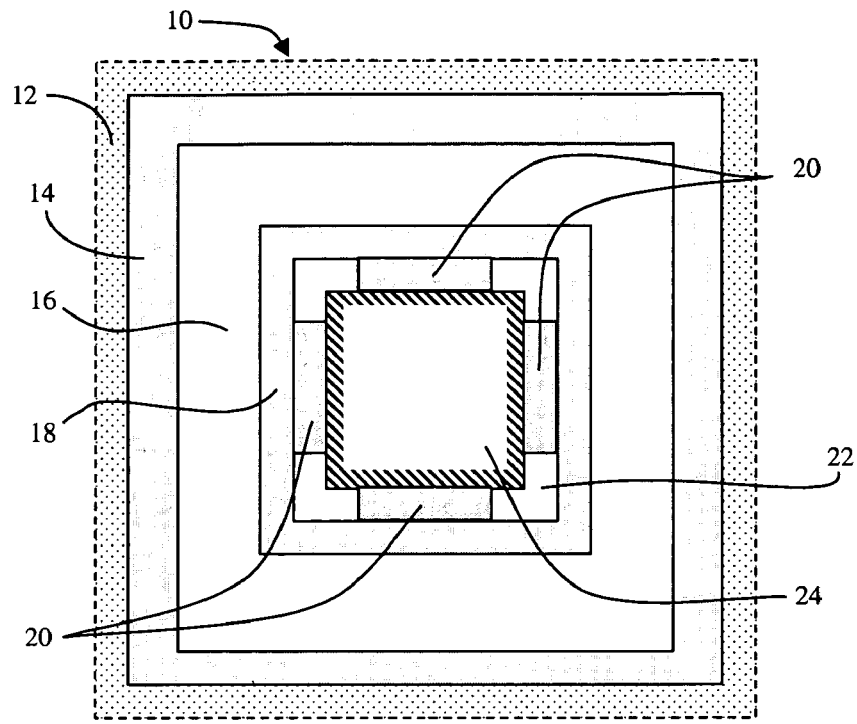
FIG. 1 is a partial cut-away view of a first embodiment of an underwater probe according to the invention.
Figure 2:
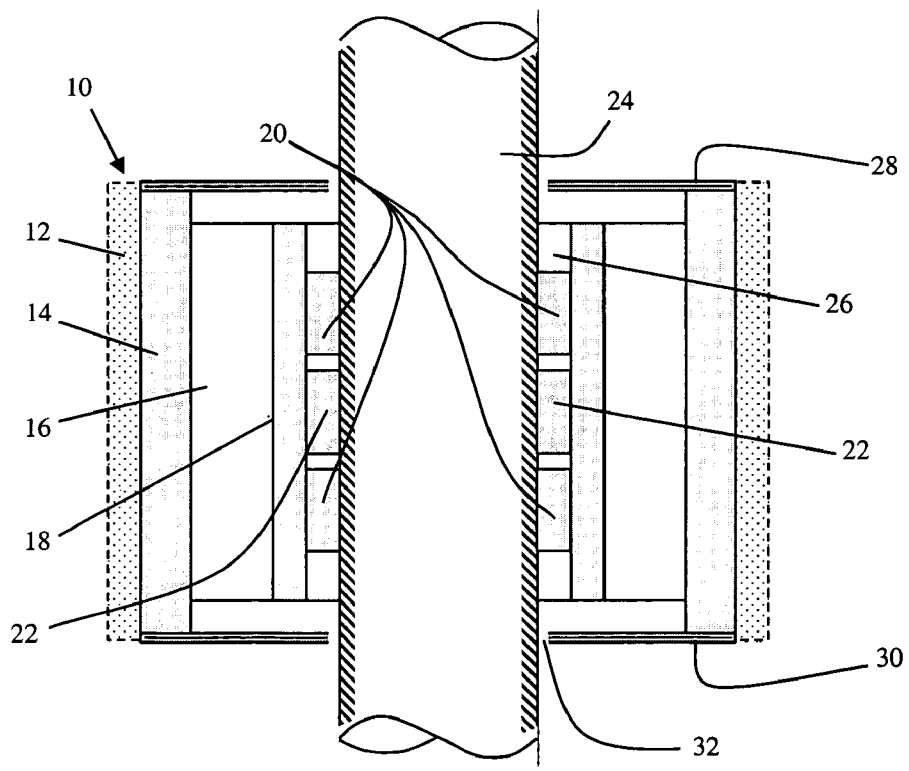
FIG. 2 is a cross sectional view of a version of the probe of FIG. 1 that functions as an underwater hybrid probe.

A probe 10 for use underwater to measure true acoustic intensity is shown generally in FIGS. 1 and 2. The outer casing of probe 10 is preferably made neutrally buoyant, such that wave vibrations affect the probe casing 14 just as they would affect the water which probe 10 displaces. Probe casing 14 may include a syntactic foam casting 12. The cured foam can be used, trimmed or weighted to achieve neutral buoyancy, as needed. While it is preferred that the outer casing be made neutrally buoyant, embodiments of the present invention may be made without a neutrally buoyant outer casing. A compliance layer 16 separates the probe outer casing 14 from a "coupling-mass" or secondary casing 18. The compliance layer may take a variety of forms, and in this embodiment is a thin layer of compliant rubber, such as a silicon rubber. A plurality of sensor elements 20 and 22 are disposed between the inner surface of the "coupling-mass" or secondary casing 18 and a central mounting structure or support 24. In this embodiment, the sensor elements are small piezoelectric wafers 20 and 22 mounted between the "coupling-mass" or secondary casing 18 and the support 24. The probe or sensor 10 is designed to be mounted to a rigid or semi rigid mounting structure such as support 24. The outer surface of the support 24 or the entire support 24 may be considered an inner sensor support, or a different sensor support may be provided.

In the embodiment of FIGS. 1 and 2, casting 12 is a rigid syntactic foam material having a density less than that of water and strong enough to withstand high hydrostatic pressure. An appropriate amount of foam is used to allow the casting 12 and the and the rest of the probe casing 14 to have the same mass as the volume of water displaced by the entire probe 10. The cured foam can be trimmed or weighted to achieve neutral buoyancy.

Acoustic pressures act to displace the casting 12 and the remainder of the probe casing 14 with the same magnitude and phase of the acoustic particle displacement. Motion of the probe casing 14 results in spring-like forces in the compliant rubber 16 which are directly applied to the "coupling-mass" or secondary casing 18. The forces generated at the casing 18 are imparted to the piezoelectric elements 20 and 22. The piezoelectric sensors 20 and 22 are preferably smaller than the inner surface of the secondary casing 18. Effectively, the entire acoustic pressure exerted on the casting 12 and probe casing 14 are coupled into the smaller area of the piezoelectric elements 20 for frequencies much higher than the resonance exhibited by the compliant rubber layer 16, the probe casing 14, and the "coupling-mass" or secondary casing 18. In this embodiment, piezoelectric elements 20 are poled in a 3-3 mode, while the elements 22 are poled in a 1-5 mode for a response to shear. The electrical signal generated by the piezoelectric elements 20 and 22 correspond to the magnitude and frequency of the sensed vibration. This voltage output is directly proportional to the neutrally buoyant probe casing's velocity which, in turn, is substantially the same as that of the surrounding water.

One novel feature of this invention is the suspension method used to fix the time-average location of the probe. Inertial-type probes of the prior art typically involve suspensions of the outer casing which must be allowed to move in concert with the acoustic wave vibrations. Generally, any suspension system will limit the response of at least one degree of freedom, if not more. However, the invention treats this probe as a pair of coupled masses, comprising the outer casing 14 and the "coupling-mass" casing 18, with the outer casing 14 mass being negligible due to the buoyancy corrections made by the syntactic foam 12. It can then easily be shown that above the resonance frequency of the combined system of the compliant layer 16, the probe casing 14, and the inner casing 18, there is essentially no motion of the inner casing 18. The present invention can exploit this fact by rigidly mounting the probe by the central support 24. This fixes the time-average location of the probe while having in essence no effect on the probe's response.

Since the neutrally buoyant outer casing moves in concert with the acoustically induced motion of water, the probe can be made small relative to the wavelength of the acoustic field. While the overall package of the intensity probe can be made much smaller than that of a prior art inertial-type probes, the non-zero length of the probe still introduces an error in the velocity measurement. It is probably not practical to make the probe smaller than about 1.5 cm, but this would still permit operation up to 25,000 Hz before acoustic scattering becomes significant.

In one embodiment of the invention, the syntactic foam casting 12 is a mixture of epoxy resin and glass microballoons. As shown in FIG. 2, the assembly of rectangular components is centered within a rectangular-shaped casting 12. Pressure sensors 28 and 30 are mounted on the edge of the casting 12, a portion of each pressure sensor 28 and 30 being directly exposed to the surrounded water and the small gap 32 is sealed with a compliant, waterproof material. Pressure hydrophones 28 and 30 can be cast into the end faces of the outer casing 14, or cemented on casting 12 after the foam has cured. An air-backed piezoceramic bender disk is an example of the type of hydrophone which can be used in probe 10.

In use, the probe 10 can be directly mounted to an external support structure via the central support rod 24 at a desired elevational measurement point and oriented in a desired measurement direction. Voltage outputs from the piezoelectric elements 20 are directly proportional to acoustic particle velocity in the plane normal to the support rod 24 while the voltage output from the piezoelectric elements 22 is proportional to the acoustic particle velocity in the direction parallel to the support rod 24. Alternatively, the voltage outputs from the pressure sensors 28 and 30 can be used to approximate the acoustic particle velocity in the direction parallel to the support rod 24 according to the equations given above. Combinations of the various signal output of the probe by those skilled in the art yield accurate measurements of the complete vector field of the acoustic intensity. This embodiment provides a probe which is compact, light in weight, easy to handle out of water, and adapts well to a variety of support structures. Also, multiple units could be combined along the same support rod 24 to create an array of probes 10. Additionally, the potentially small size can greatly reduce the effect of acoustic field scattering.

Figure 3:
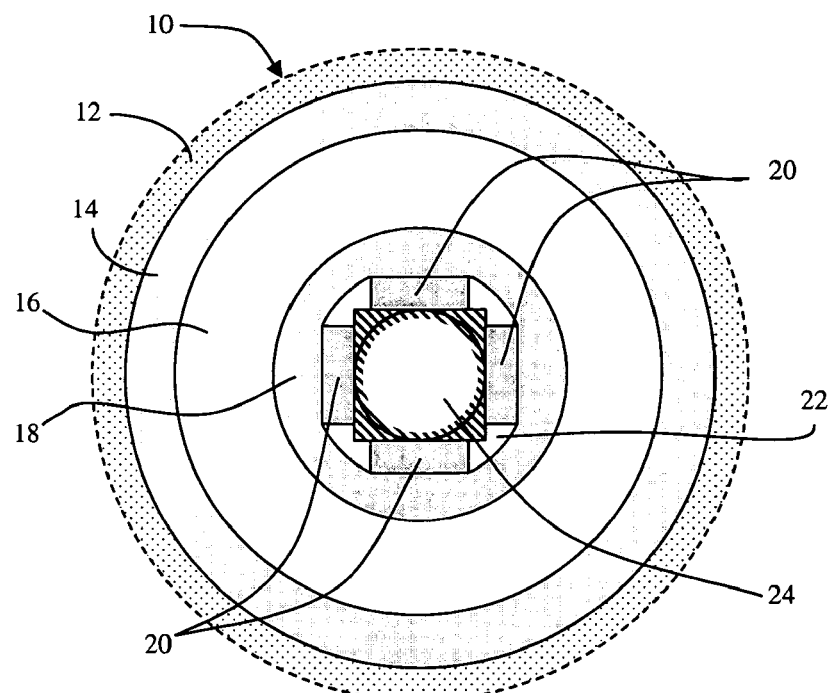
FIG. 3 is a partial cut-away view of a second embodiment of an underwater probe according to the invention.
Figure 4:
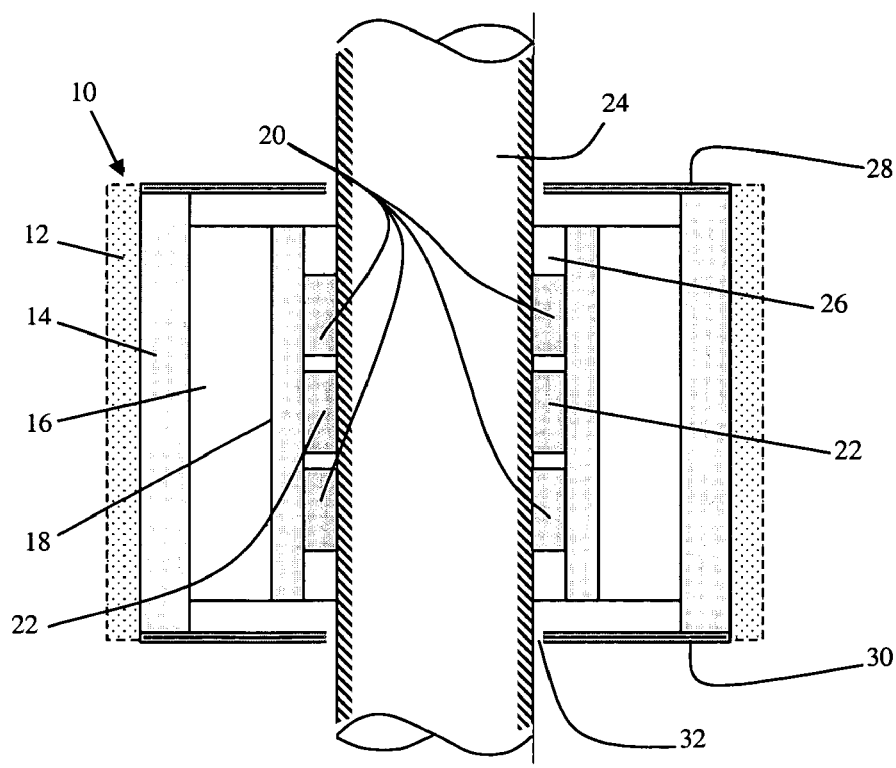
FIG. 4 is a cross sectional view of a version of the probe of FIG. 3 that functions as an underwater hybrid probe.

A second embodiment is shown in FIGS. 3 and 4, in which the probe 10 consists of a plurality of cylindrical layers, rather than square-shaped as indicated in FIGS. 1 and 2. This embodiment is constructed in a similar manner and exhibits roughly the same properties as the first embodiment. The same reference numbers are used for corresponding elements. The outer casing 14 can be more easily adapted to an acoustic pressure means by simply using a piezoelectric cylinder of appropriate dimensions. Also, the cylindrical profile further reduces acoustic scattering of the field.

Figure 5:
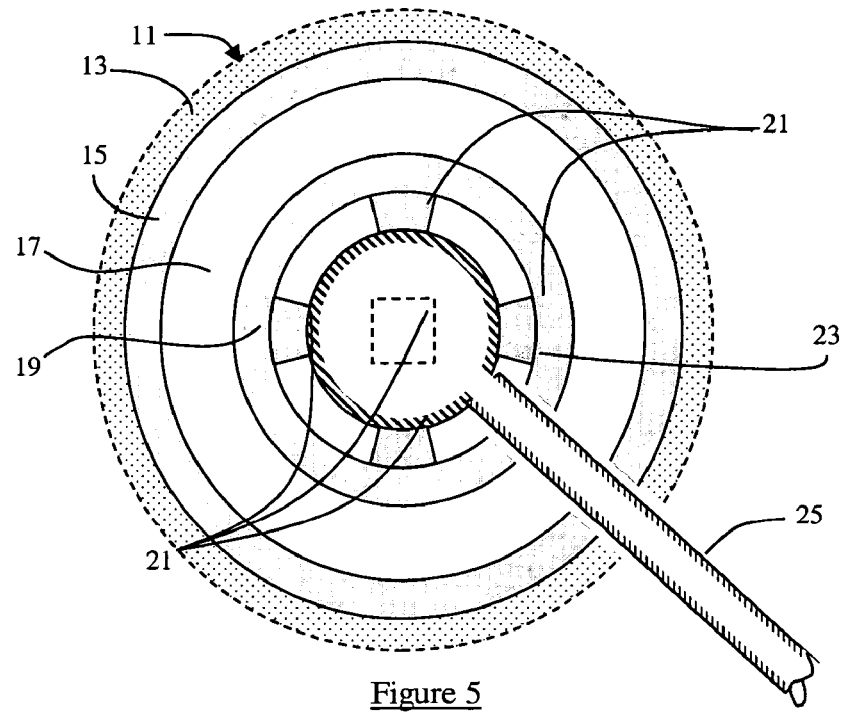
FIG. 5 is a partial cut-away view of a third embodiment of an underwater probe according to the invention.
Figure 6:
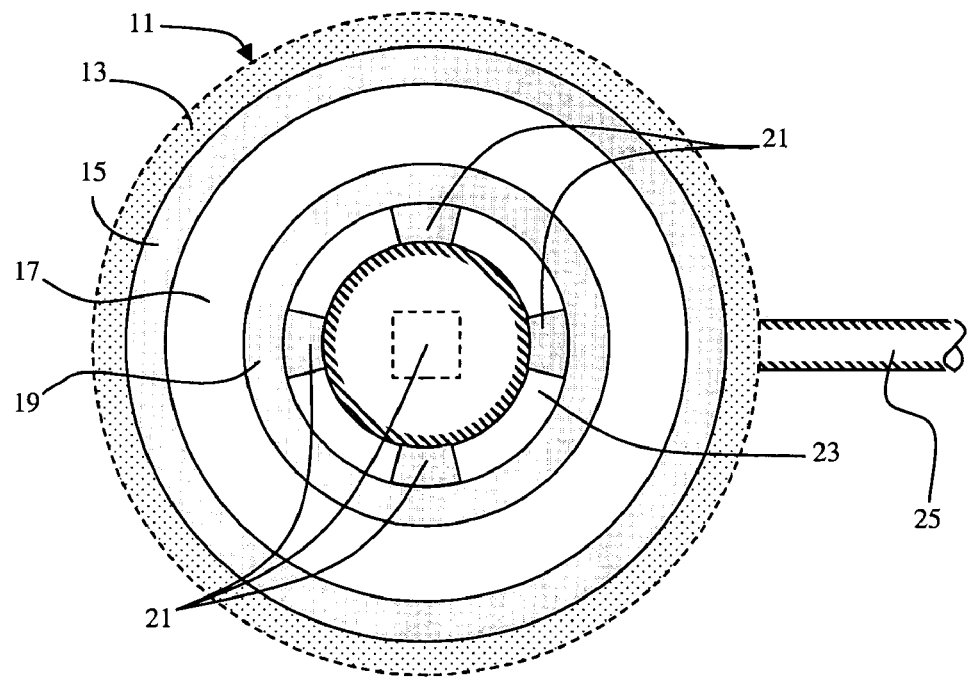
FIG. 6 is another partial cut-away view of the third embodiment of an underwater probe according to the invention.

A third embodiment is shown in FIGS. 5 and 6, in which the probe 11 consists of a plurality of spherical layers, rather than cylindrical as describe above. In this embodiment, the foam casing 13 encloses a thin walled piezoelectric sphere 15. This in turn encloses a thin layer of compliant rubber 17 and a smaller "coupling-mass" sphere 19 to which are bonded a plurality of six small piezoelectric wafers 21 and a central rigid sphere-rod assembly 25. The piezoelectric wafers 21 are positioned in pairs along orthogonal Cartesian axes such that the average location of the pairs is co-located at the center of the probe 11. The rigid sphere-and-rod support 25 is oriented such that it emerges from the probe 11 at an angle of forty-five degrees with respect to the axes established by the piezoelectric element 21 pairs so as not to interfere with location of the piezoelectric elements 21.

Signals incident on probe 11 will cause motion of the casting 13 and piezoelectric shell or casing 15. The acoustic pressure of the incident wave is directly measured by the piezoelectric shell 15. The acoustic forces on the sphere are coupled into the piezoelectric elements 21 identically as described in the first embodiment. However, in this third embodiment, the outer casing 15 is free to move in three-dimensions, i.e. there is no restriction on its motion due to the support provided by the central sphere-and-rod support 25. The piezoelectric elements 25 are electrically connected in pairs such that each pair outputs a voltage proportional to the acoustic particle acceleration in the direction along the separation vector between them, but produces no output for compressional forces on the element pairs. Thus, the probe 11 directly measures the acoustic pressure and the acoustic particle acceleration in three orthogonal directions. A pressure signal from sensor 15 and the appropriate velocity signal from piezoelectric elements 21 are combined to provide the true acoustic intensity.

Figure 7:
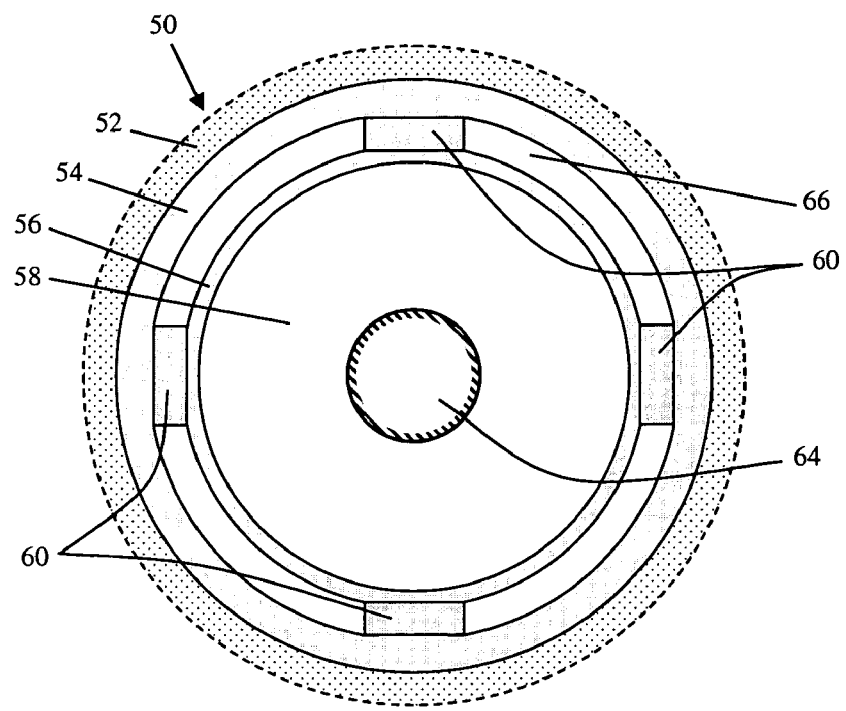
FIG. 7 is a partial cut-away view of a fourth embodiment of an underwater probe according to the invention.
Figure 8:
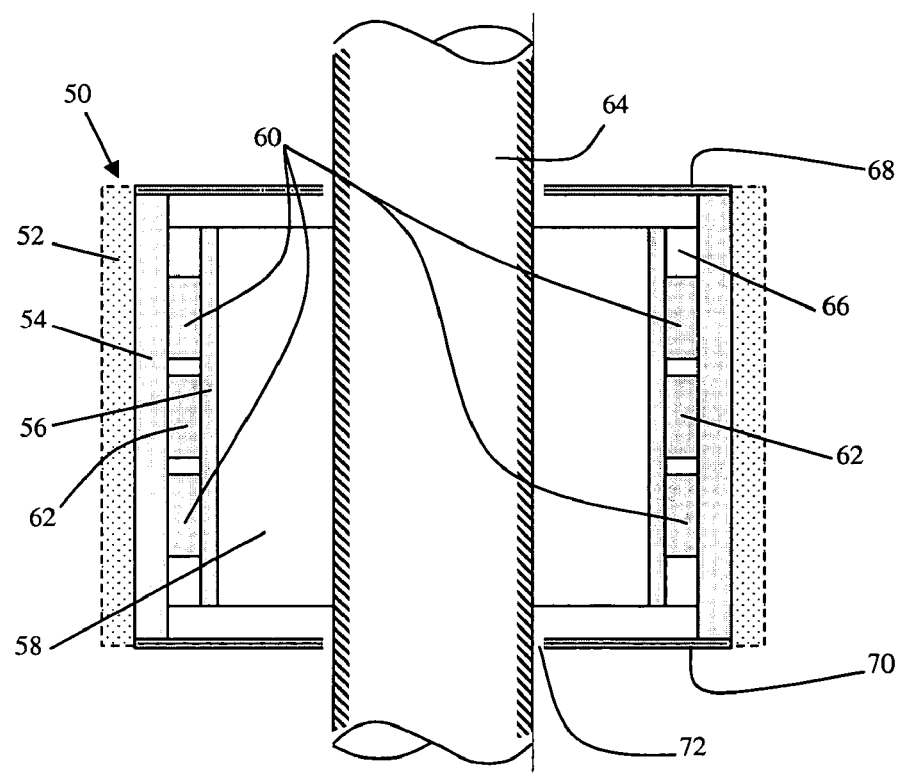
FIG. 8 is a cross sectional view of a version of the probe of FIG. 7 that functions as an underwater hybrid probe.

Further, a fourth embodiment of the probe 50 is shown in FIGS. 7 and 8, in which the compliant layer 58 and the piezoelectric elements 60 and 62 are reversed as compared to the previously noted embodiments. In this embodiment, neutral buoyancy requires the displaced water mass to be equal to the combined mass of the casting 52, the outer casing 54, the "coupler mass" casing 56 and the elements 60 and 62, in order that rigidly mounting the center support has no effect on the sensor response. Other details are consistent with previously detailed embodiment descriptions noted above, for example 1-5 shear piezoelectric elements 62 may be removed and two hydrophones 68 and 70 may be used to approximate the velocity parallel to the central support. Any gaps 72 should be sealed with a highly compliant material. The voltage output of the piezoelectric elements 60 and 62 are directly proportional to the three dimensional acoustic particle acceleration, rather than particle velocity. The output voltage signals can be electrically corrected to be proportional to the particle velocity and then combined with the acoustic pressure signal to compute acoustic intensity of the field. In this configuration, the probe has a slightly higher response to acoustic excitation as compared to above the detailed embodiments.

Various modifications can be made to the embodiments described herein. For example, the use of syntactic foam is required solely for balancing buoyant forces on the probe and may or may not be necessary in some embodiments of a probe. Any rigid material is suitable as a casting or housing around the velocity sensor provided the density of the sensor is the same as the fluid in which measurements are to be made. Alternatively, the sensor can be made more or less dense than the fluid it displaces, and a sensor transfer function can be determined and taken into account in acoustic intensity calculations. This can be accomplished by calibrating the output of the sensor to a known acoustic velocity field, such as a plane progressive wave. Also, probe 10, 11 or 50 can produce pressure and velocity signals to be recorded separately for later processing. Alternatively, simple electronic circuitry (not shown) could be cast into castings 12, 13 or 52, or contained within the rigid support rod 24, 25 or 64, so that acoustic intensity can be calculated within probe 10, 11 or 50. Another alternative is to connect the signal output leads to an external device (i.e. digital signal analyzer) to calculate acoustic intensity.

As will be clear to those of skill in the art, other modifications may also be made. As mentioned previously, the layer of compliant material in the described embodiments may be replaced with other compliance layers. The illustrated layer of compliant silicon rubber is continuous and completely encases the secondary casing or inner support. Alternatively, there can be gaps in the layer, or springs or other compliance elements may be used to form the compliance layer. When silicon rubber is used, it is preferred that it be highly compliant, especially in comparison to the generally rigid outer and secondary casings. In some embodiments, the compliant material has a Shore A hardness less than 50, while other embodiments have a hardness less than 30, and still other have a compliance less than 20. One version has a hardness of approximately 10. As will be clear to those of skill in the art, a similar effective compliance may be obtained with harder materials if voids are provided, or through other approaches. In some embodiments, the compliance layer has a thickness of 2-4 millimeters, though thicker and thinner layers could be used. The outer and secondary casings may be formed of various materials, with some versions being made of aluminum. Outer casings made of piezoelectric material are another possibility, as discussed above. The piezoelectric elements may take a variety of forms, such as being peizoceramic.

Many other modifications and variations of the invention are possible in view of the above disclosure. It is therefore to be understood that the invention may be practiced otherwise than as specifically described, without departing from the scope or teaching of this invention.

We claim:

1. An underwater acoustic sensor for attachment to a rigid or semi rigid mounting structure, the sensor comprising:
    a generally rigid outer casing having an inner surface and an outer surface;
    a generally rigid secondary casing spaced from the outer casing, the secondary casing having an inner surface and an outer surface;
    a compliance layer disposed between the inner surface of the outer casing and the outer surface of the secondary casing;
    an inner sensor support configured for direct attachment to the mounting structure, the sensor support spaced from the inner surface of the secondary casing; and
    a plurality of sensor elements disposed between and interconnecting the inner surface of the secondary casing and the sensor support.

2. The sensor according to claim 1, wherein the sensor elements are each piezoelectric elements.

3. The sensor according to claim 2, wherein some of the piezoelectric elements are poled to sense shear and some of the piezoelectric elements are poled to sense compression or tension.

4. The sensor according to claim 1, wherein the sensor elements comprise a system of independent pairs or groups of piezoelectric elements operable to provide a signal proportional to the three independent orthogonal components of acoustic particle velocity due to motion of the outer casing.

5. The sensor according to claim 1, wherein the sensor has a useful frequency range, the resonance frequency of the outer casing, compliant layer and secondary casing being lower than the useful frequency range.

6. The sensor according to claim 1, wherein the outer casing and the secondary casing each have a shape selected from a group consisting of generally cylindrical, generally rectangular, and generally spherical.

7. The sensor according to claim 6, wherein the sensor support has a generally rectangular outer surface.

8. The sensor according to claim 1, wherein the compliance layer comprises a layer of compliant material.

9. The sensor according to claim 8, wherein the compliant material is a silicone rubber.

10. The sensor according to claim 1, wherein the outer casing is neutrally buoyant.

11. The sensor according to claim 10, wherein the outer casing includes a generally rigid inner portion and a generally rigid foam covering at least part of the inner portion.

12. The sensor according to claim 1, further comprising a pressure sensor disposed on the outer surface of the outer casing.

13. The sensor according to claim 12, wherein the outer casing is generally cylindrical with a pair of opposed end faces, the pressure sensor comprising a pressure sensor disposed on each of the opposed end faces of the outer casing.

14. The sensor according to claim 1, wherein the outer casing is at least partially formed of a piezoelectric material such that it is operable as a pressure sensor.

15. The sensor according to claim 1, further comprising circuitry for processing signals from the sensor elements.

16. The sensor according to claim 1, wherein the sensor support comprises an outer surface of the rigid or semi rigid mounting structure.

17. An underwater acoustic sensor for attachment to a rigid or semi rigid mounting structure, the sensor comprising:
a generally rigid outer casing having an inner surface and an outer surface;
a generally rigid secondary casing spaced from the outer casing, the secondary casing having an inner surface and an outer surface;
a plurality of sensor elements disposed between and interconnecting the inner surface of the outer casing and the outer surface of the secondary casing;
an inner sensor support configured for direct attachment to the mounting structure, the sensor support spaced from the inner surface of the secondary casing; and
a compliance layer disposed between the inner surface of the secondary casing and the sensor support.

18. The sensor according to claim 1, wherein the combination of the outer casing, inner casing and sensor elements is neutrally buoyant.

19. The sensor according to claim 17, further comprising a pressure sensor disposed on the outer surface of the outer casing.

20. The sensor according to claim 17, wherein the outer casing is at least partially formed of a piezoelectric material such that it is operable as a pressure sensor.

21. An underwater sensor array comprising:
a mounting structure having an outer surface, the mounting structure being rigid or semi-rigid;
a plurality of underwater sensors disposed on the mounting structure, each sensor comprising:
a generally rigid outer casing having an inner surface and an outer surface;
a generally rigid secondary casing spaced from the outer casing, the secondary casing having an inner surface and an outer surface;
a compliance layer disposed between the inner surface of the outer casing and the outer surface of the secondary casing; and
a plurality of sensor elements disposed between and interconnecting the inner surface of the secondary casing and the outer surface of the mounting structure,
the mounting structure acting as a sensor support for the plurality of sensor elements.

* * * * *